United States Patent [19]

Spangler et al.

[11] Patent Number: 5,670,691
[45] Date of Patent: Sep. 23, 1997

US005670691A

[54] METHOD FOR MAKING A SUBSTITUTED BENZENE COMPOUND

[75] Inventors: Lori Ann Spangler, Churchville; Damian Gerard Weaver, Lansdale, both of Pa.

[73] Assignee: Rohm and Haas Company, Philadelphia, Pa.

[21] Appl. No.: 524,821

[22] Filed: Sep. 7, 1995

Related U.S. Application Data

[63] Continuation-in-part of Ser. No. 324,655, Oct. 18, 1994, abandoned.

[51] Int. Cl.$^6$ .............................. C07C 303/40; C07F 9/02
[52] U.S. Cl. ................................ 558/56; 558/57; 558/58; 558/45
[58] Field of Search .................................. 558/56, 57, 58, 558/45

[56] References Cited

PUBLICATIONS

Courtin et al., Helv. Chim. Acta, 60(3), 19–26 (1977). 1977.
Bamfield et al., J. Chem. Perk. Trans. II, 11, 691–696 (1988). 1988.
Figuly et al., J. Org. Chem., 45, 3728–29 (1980). 1980.
Alo et al., J. Chem. Perk. Trans. I, 6, 1611–14 (1990). 1990.

*Primary Examiner*—Johann Richter
*Assistant Examiner*—Laura R. Cross
*Attorney, Agent, or Firm*—Clark R. Carpenter

[57] ABSTRACT

A method for making a substituted benzene compound includes reacting a 2-substituted benzenesulfonate or the 2-substituted benzenesulfonate further substituted in the 3, 4 or 5-position with a lithium compound to form an intermediate; and reacting the intermediate with an electrophile to form a 2,6-disubstituted benzenesulfonate or a 2,6-disubstituted benzenesulfonate further substituted in the 3, 4 or 5-position.

13 Claims, No Drawings

METHOD FOR MAKING A SUBSTITUTED BENZENE COMPOUND

This application is a continuation in-part of U.S. application Ser. No. 08/324,655 filed Oct. 18, 1994, now abandoned.

The present invention is directed to a method for making a substituted benzene compound, more specifically, a method for making a 2,6-disubstituted benzenesulfonate or a 2,6-disubstituted benzenesulfonate further substituted in the 3, 4 or 5-position.

Ortho-metalation of alkyl arenesulfonates to provide 2-substituted and 2,4-disubstituted alkyl arenesulfonates has been reported, see "Directed Ortho-Lithiation of Alkyl Arenesulfonates", J. N. Bonfiglio, *J. Org. Chem.* 1986, 51, 2833–2835. However, Bonfiglio is silent with respect to methods for making a 2,6-substituted alkyl arenesulfonate.

A method for making a substituted benzene compound which comprises reacting a 2-substituted benzenesulfonate or a 2-substituted benzenesulfonate, further substituted in the 3, 4 or 5-position, with a lithium compound to form an intermediate compound; and reacting the intermediate compound with an electrophile to form a 2,6-disubstituted benzenesulfonate or a 2,6-disubstituted benzenesulfonate further substituted in the 3, 4 or 5-position. The 2,6-disubstituted benzenesulfonates or 2,6-disubstituted benzenesulfonates further substituted in the 3, 4 or 5-position made by the method of the present invention are useful as intermediates in a method for making certain compounds known to be useful as herbicides, for example, the phosphosulfonate compounds disclosed in U.S. Pat. No. 5,272,128 and the sulfonyl urea compounds disclosed in U.S. Pat. No. 4,127,405.

In a preferred embodiment, the 2-substituted benzenesulfonate or the 2-substituted benzenesulfonate further substituted in the 3, 4 or 5-position is a compound having the structural formula (1):

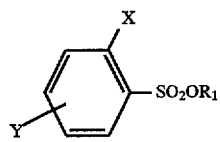

wherein:

$R_1$ is alkyl, cycloalkyl or phenyl;

X is any group that is not reactive with the lithium compound under the reaction conditions used; and Y is any group in the 3, 4 or 5-position that is not reactive with the lithium compound under the reaction conditions used.

In a preferred embodiment, $R_1$ is $(C_2-C_5)$alkyl and, more preferably, isopropyl.

In a preferred embodiment, X is fluoro, chloro, alkoxy, more preferably $(C_1-C_3)$alkoxy, haloalkyl, more preferably halo$(C_1-C_3)$alkyl, haloalkoxy, more preferably halo$(C_1-C_3)$alkoxy, alkyl, more preferably $(C_1-C_4)$alkyl, alkylthio, more preferably $(C_1-C_4)$alkylthio, haloalkylthio, more preferably halo$(C_1-C_4)$alkylthio, or N,N-dialkylcarboxamide, more preferably N,N-di$(C_2-C_4)$alkylcarboxamide.

In a highly preferred embodiment, X is chloro, fluoro, methoxy, trifluoromethyl, pentafluoroethyl, methylthio, ethylthio or trifluoromethoxy.

In a preferred embodiment, Y is a hydrogen atom, fluoro, chloro, alkoxy, more preferably $(C_1-C_3)$alkoxy, haloalkyl, more preferably halo$(C_1-C_3)$alkyl, haloalkoxy, more preferably halo$(C_1-C_3)$alkoxy, alkylthio, more preferably $(C_1-C_4)$alkylthio, or haloalkylthio, more preferably halo$(C_1-C_4)$alkylthio.

In a highly preferred embodiment, Y is a hydrogen atom, chloro, fluoro, methoxy, trifluoromethyl, trifluoromethoxy, pentafluoroethyl, methylthio or ethylthio.

"Alkyl" means a straight or branched alkyl chain and includes, for example, methyl, ethyl, n-propyl, isopropyl, n-butyl, sec-butyl tert-butyl, n-pentyl, n-hexyl. "Cycloalkyl" means a monocyclic non-aromatic alkyl ring and includes, for example, cyclobutyl, cyclopentyl, cyclohexyl. "Alkoxy" means a linear or branched alkoxy group and includes, for example, methoxy, ethoxy, isopropoxy and n-propoxy. "Alkylthio" means a linear or branched alkyl group attached to a sulfur atom and includes, for example, methylthio, ethylthio, isopropylthio and n-propylthio. "Haloalkyl" means a linear or branched alkyl group substituted with one or more halogen atoms and includes, for example, trifluoromethyl, perfluoroethyl and 2,2,2-trifluoroethyl. "Haloalkoxy" means a linear or branched alkoxy group substituted with one or more halogen atoms and includes, for example, trifluoromethoxy, perfluoroethoxy and chloromethoxy. "Haloalkylthio" means a linear or branched alkyl group, substituted with one or more halogen atoms, attached to a sulfur atom and includes, for example, trifluoromethylthio, perfluoroethylthio and chloromethylthio. "N,N-Dialkyl carboxamide" means a carboxamide group wherein the nitrogen atom is substituted with two alkyl groups and includes, for example, diethylcarboxamide and diisopropylcarboxamide.

Suitable lithium compounds are those lithium compounds that are sufficiently strong bases to remove a proton having a pKa of 30–37 and include, for example, elemental lithium as well as organolithium compounds such as, for example, $(C_1-C_6)$alkyl lithiums and aryl lithiums. "$(C_1-C_6)$alkyl lithium" means an alkyl lithium compound having from 1 to 6 carbon atoms per molecule, and includes, for example, butyl lithium, hexyl lithium and methyl lithium. "Aryl lithium" means an aromatic organolithium species, and includes, for example, phenyl lithium, and thienyl lithium.

While not wishing to be bound by theory, it is believed that the intermediate formed in the first step of the method of the present invention is an organolithium intermediate having the structural formula (2):

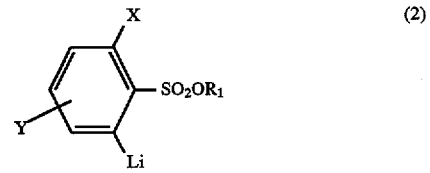

wherein $R_1$, X and Y are defined as above.

Suitable electrophiles are those compounds that react to form a covalent bond with an anionic intermediate such as compound (2) and that do not contain an acidic proton which can be deprotonated by an anionic intermediate such as compound (2). In a preferred embodiment, the electrophile is selected from the group consisting of alkyl halides, haloalkyl alkyl ethers, aldehydes, ketones, alkyl sulfates, boron esters, alkyl disulfides, deuterium oxide, dimethylformamide, N-formylpiperidine, carbon dioxide, trialkylsilyl chlorides, and sources of positive halogens. Suitable alkyl halides include, for example, iodomethane, iodoethane and iodopropane. Suitable haloalkyl alkyl ethers include, for example, bromomethyl methyl ether. Suitable aldehydes include, for example, formaldehyde, and benzaldehyde. Suitable ketones include, for example, benzophenone. Suitable alkyl sulfates include, for example, dimethylsulfate. Suitable boron esters include, for example, trimethyl borate and triisopropyl borate. Suitable alkyl disulfides include, for example, methyl disulfide, ethyl disulfide and phenyl disulfide. Suitable trialkylsilyl chlorides include, for example, trimethylsilyl chloride. Suitable sources of positive halogens include, for example, N-fluorobenzenesulfonimide, N-fluoro-O-benzenedisulfonimide, N-fluoropyridinium salts, N-chlorosuccinimide, and 2,2,2-trifluoroethyl iodide.

Any anhydrous, aprotic solvent may be used in the steps wherein the 2-substituted benzenesulfonate or the 2-substituted benzenesulfonate further substituted in the 3, 4 or 5-position is reacted with a lithium compound to form an intermediate and the intermediate is reacted with an electrophile to form the 2,6-disubstituted benzenesulfonate or the 2,6-disubstituted benzenesulfonate further substituted in the 3, 4 or 5-position. Suitable aprotic solvents include, for example, ethers such as, for example, diethyl ether and ethylene glycol dimethyl ether, including cyclic ethers such as, for example, tetrahydrofuran and dioxane, and alkanes, such as, for example, hexane, heptane and pentane, and aromatic solvents such as, for example, cumene, as well as mixtures thereof. In a preferred embodiment, the solvent is tetrahydrofuran or a mixture of tetrahydrofuran and hexane. In a more highly preferred embodiment, the solvent is a mixture of tetrahydrofuran and hexane that includes from 1 to 4 milliliters (mL) of tetrahydrofuran per millimole (mmole) of the 2-substituted benzenesulfonate or the 2-substituted benzenesulfonate further substituted in the 3, 4 or 5-position and from 0.25 to 3 mL of hexane per mmole of the 2-substituted benzenesulfonate or the 2-substituted benzenesulfonate further substituted in the 3, 4 or 5-position.

In a preferred embodiment, an oxygen-free atmosphere is used in the steps wherein the 2-substituted benzenesulfonate or the 2-substituted benzenesulfonate further substituted in the 3, 4 or 5-position is reacted with a lithium compound to form an intermediate and the intermediate is reacted with an electrophile to form the 2,6-disubstituted benzenesulfonate or the 2,6-disubstituted benzenesulfonate further substituted in the 3, 4 or 5-position.

The step of the present method wherein the 2-substituted benzenesulfonate or the 2-substituted benzenesulfonate further substituted in the 3, 4 or 5-position is reacted with a lithium compound to form an intermediate is conducted at any convenient temperature and is preferably conducted at a temperature of from about −78° C. to about 0° C.

The step of the present method wherein the intermediate is reacted with an electrophile to form the 2,6-disubstituted benzenesulfonate or the 2,6-disubstituted benzenesulfonate further substituted in the 3, 4 or 5-position is conducted at any convenient temperature at which the intermediate is stable and is preferably conducted at a temperature of from about −78° C. to room temperature, i.e., about 25° C.

The 2,6-disubstituted benzenesulfonate or the 2,6-disubstituted benzenesulfonate further substituted in the 3, 4 or 5-position made by the method of the present invention is a compound having the structural formula (3):

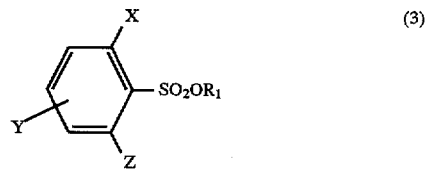

(3)

wherein $R_1$, X and Y are defined as above and Z is the residue of the electrophile.

In a preferred embodiment, Z is alkyl, more preferably $(C_1-C_6)$alkyl, alkoxy alkyl, methyleneoxy, substituted methyleneoxy, boronic acid, alkylthio, more preferably $(C_1-C_3)$alkylthio, phenyl, a deuterium atom, formyl, carboxyl, trialkylsilyl, more preferably tri$(C_1-C_4)$alkylsilyl, or halo.

It is noteworthy that the method of the present invention allows selective preparation of a 2,6-disubstituted benzenesulfonate or a 2,6-disubstituted benzenesulfonate further substituted in the 3, 4 or 5-position from a 2-substituted benzenesulfonate or a 2-substituted benzenesulfonate further substituted in the 3, 4 or 5-position wherein the group in the 2 position can a strongly ortho-directing group, such as, for example, trifluoromethyl, methoxy, trifluoromethoxy, and fluoro.

The 2,6-disubstituted benzenesulfonate or the 2,6-disubstituted benzenesulfonate further substituted in the 3, 4 or 5-position product may be isolated from the reaction mixture by known techniques, such as, for example, extraction.

The steps of the present invention wherein the 2-substituted benzenesulfonate or the 2-substituted benzenesulfonate further substituted in the 3, 4 or 5-position is reacted with a lithium compound to form an intermediate and the intermediate is reacted with an electrophile to form the 2,6-disubstituted benzenesulfonate or the 2,6-disubstituted benzenesulfonate further substituted in the 3, 4 or 5-position typically produces a mixture of the desired 2,6-disubstituted benzenesulfonate or the 2,6-disubstituted benzenesulfonate further substituted in the 3, 4 or 5-position and a small amount of the unreacted 2-substituted benzenesulfonate or the 2-substituted benzenesulfonate further substituted in the 3, 4 or 5-position starting material. In a preferred embodiment, the product mixture is isolated from the unreacted material by: selectively hydrolyzing the 2,6-disubstituted benzenesulfonate or the 2,6-disubstituted benzenesulfonate further substituted in the 3, 4 or 5-position of the product mixture to form a salt of the 2,6-disubstituted benzenesulfonate or a salt of the 2,6-disubstituted benzenesulfonate further substituted in the 3, 4 or 5-position; partitioning the product mixture between an aqueous phase and an organic phase; and isolating the 2,6-disubstituted benzenesulfonate or the 2,6-disubstituted benzenesulfonate further substituted in the 3, 4 or 5-position salt from the aqueous phase.

In a preferred embodiment, the 2,6-disubstituted benzenesulfonate or the 2,6-disubstituted benzenesulfonate further substituted in the 3, 4 or 5-position is selectively hydrolyzed by adding a source of hydroxyl anions, such as, for example, an aqueous solution of a metal or ammonium hydroxide or a metal carbonate, to the mixture of 2,6-disubstituted benzenesulfonate or the 2,6-disubstituted benzenesulfonate further substituted in the 3, 4 or 5-position and 2-substituted benzenesulfonate or the 2-substituted benzenesulfonate further substituted in the 3, 4 or 5-position. In a more highly preferred embodiment, the 2,6-disubstituted benzenesulfonate or the 2,6-disubstituted benzenesulfonate further substituted in the 3, 4 or 5-position is selectively hydrolyzed by adding from about one equivalent to about three equivalents of hydroxide per mole of 2,6-disubstituted benzenesulfonate or the 2,6-disubstituted benzenesulfonate further substituted in the 3, 4 or 5-position to the mixture of 2,6-disubstituted benzenesulfonate or the 2,6-disubstituted benzenesulfonate further substituted in the 3, 4 or 5-position and 2-substituted benzenesulfonate or the 2-substituted benzenesulfonate further substituted in the 3, 4 or 5-position.

The 2,6-disubstituted benzenesulfonate or the 2,6-disubstituted benzenesulfonate further substituted in the 3, 4 or 5-position may then be further reacted according to known techniques, for example, the 2,6-disubstituted benzenesulfonate or the 2,6-disubstituted benzenesulfonate further substituted in the 3, 4 or 5-position may be:

- desulfonated, for example, by treatment with sulfuric acid and a catalytic metal salt, such as a mercury salt, to form the corresponding 1,3-disubstituted benzene or a 1,3-disubstituted benzene further substituted in the 4, 5 or 6-position;
- hydrolyzed, for example, by treatment with aqueous acid or aqueous base followed by acid, to form the corresponding 2,6-disubstituted benzenesulfonic acid or the salt of a 2,6-disubstituted benzenesulfonic acid, or, the corresponding 2,6-disubstituted benzenesulfonic acid or the salt of a 2,6-disubstituted benzenesulfonic acid further substituted in the 3, 4 or 5-position; or
- converted, for example, by treatment with phosphorus oxychloride, to the corresponding 2,6-disubstituted benzenesulfonyl chloride or corresponding 2,6-disubstituted benzenesulfonyl chloride further substituted in the 3, 4 or 5-position.

In a preferred embodiment, the 2,6-disubstituted benzenesulfonate or the 2,6-disubstituted benzenesulfonate further substituted in the 3, 4 or 5-position is made according to the above described method, the 2,6-disubstituted benzenesulfonate or the 2,6-disubstituted benzenesulfonate further substituted in the 3, 4 or 5-position so formed is hydrolyzed and isolated as the corresponding 2,6-disubstituted benzenesulfonate or the 2,6-disubstituted benzenesulfonate further substituted in the 3, 4 or 5-position salt, the salt is then converted to the corresponding 2,6-disubstituted benzenesulfonyl chloride or corresponding 2,6-disubstituted benzenesulfonyl chloride further substituted in the 3, 4 or 5-position and the 2,6-disubstituted benzenesulfonyl chloride or corresponding 2,6-disubstituted benzenesulfonyl chloride further substituted in the 3, 4 or 5-position is then reacted with a hydroxymethylphosphorus compound to form a phosphosulfonate compound.

In a highly preferred embodiment of the present invention, the 2,6-disubstituted benzenesulfonyl chloride or corresponding 2,6-disubstituted benzenesulfonyl chloride further substituted in the 3, 4 or 5-position is reacted with a hydroxymethylphosphorus compound of structural formula (4):

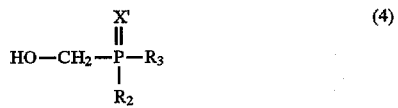

wherein:

X' is an oxygen or a sulfur atom, and $R_2$ and $R_3$ are each independently substituted or unsubstituted alkyl, alkoxy, alkylthio, alkenyloxy, alkynyloxy, haloalkoxy, cyanoalkoxy, alkoxyalkoxy, cycloalkoxy, cycloalkylalkoxy, alkylideneiminooxy, amino, phenyl or phenoxy; or $R_2$ and $R_3$ are both alkoxy, taken together with the phosphorus atom to form a six-membered oxygen-containing ring, to form a phosphosulfonate compound of the structural formula (5):

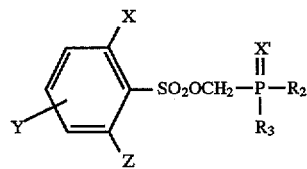

wherein X, X', Y, Z, $R_2$ and $R_3$ are each defined as set forth above.

"Alkenyloxy" means an oxygen atom substituted with a straight or branched alkenyl chain and includes, for example, allyloxy. "Alkynyloxy" means an oxygen atom substituted with a straight or branched alkynyl chain and includes, for example, propargyloxy. "Cyanoalkoxy" means a straight or branched alkoxy chain substituted with a cyano group and includes, for example, cyanomethoxy. "Cycloalkoxy" means an oxygen atom substituted with a cycloalkyl group and includes, for example, cyclobutoxy and cyclopentoxy. "Cycloalkylalkoxy" means a straight or branched alkoxy chain substituted with a cycloalkyl group and includes, for example, cyclopropylmethoxy. "Alkylideneiminooxy" refers an alkyl group doubly bonded to a nitrogen atom which is in tern bonded to an oxygen atom and includes, for example, isopropylideneiminooxy.

Reaction between the 2,6-disubstituted benzenesulfonyl chloride or corresponding 2,6-disubstituted benzenesulfonyl chloride further substituted in the 3, 4 or 5-position and the hydroxymethylphosphorus compound can be carried out under various conditions, for example, in the presence of an organic solvent and an amine base; or in a phase transfer catalyzed reaction wherein the coupling takes place in a two-phase solvent system in the presence of an aqueous base solution and a phase transfer catalyst such as triethylbenzylammonium chloride; or the anion of the hydroxymethylphosphorus compound can be formed with a strong base such as sodium hydride or sodium, then the anion reacted with the 2,6-disubstituted benzenesulfonyl chloride or corresponding 2,6-disubstituted benzenesulfonyl chloride further substituted in the 3, 4 or 5-position, as disclosed in U.S. Pat. No. 5,272,128.

A first phosphosulfonate compound of structural formula (5) wherein $R_2$ is an alkoxy group and $R_3$ is an alkoxy or an alkyl group can be converted to a second phosphosulfonate of structural formula (5) that is substituted with, for example, an amino, alkylthio or an alkoxy group different from that of the first phosphosulfonate compound, via a phosphonyl chloride or phosphinoyl chloride intermediate by, for example, treating the first phosphosulfonate compound with, for example, phosphorus pentachloride or thionyl chloride, to form the phosphonyl chloride or phosphinoyl chloride intermediate and then treating the intermediate with, for example, an alcohol, a disubstituted amine or an alkyl mercaptan to yield the second phosphonyl chloride compound.

The following examples and tables are provided merely to illustrate the method of the present invention and the compounds resulting therefrom and are not intended to limit the scope of the present invention which is defined by the claims.

EXAMPLE 1A

Preparation of isopropyl 2-trifluoromethyl-6-methylbenzenesulfonate

A solution of 400 grams (g) of 2-trifluoromethylbenzenesulfonyl chloride in 600 milliliters (mL) of isopropanol was cooled in an ice bath and treated with a solution of 180 mL of pyridine in 200 mL of isopropanol at a rate to keep the internal temperature <10° C. The mixture was maintained at 0°–5° C. for 24 hours, then treated with 1 liter (L) of ether. The slurry was filtered and the solvent removed from the filtrate in vacuo. To the filtrate was added 800 mL of ether and the resulting mixture was washed with 500 mL portions of 5% aqueous hydrochloric acid, water, saturated aqueous sodium bicarbonate, water, and then brine. The organic phase was dried through calcium sulfate and the solvent removed in vacuo to yield 306 g isopropyl 2-trifluoromethylbenzenesulfonate as an oil.

A solution of 100 g of isopropyl 2-trifluoromethylbenzenesulfonate in 1 L of dry tetrahydrofuran was cooled to −78° C. under a static nitrogen atmosphere. To this was added 257 mL of a 1.6 molar (M) solution of n-butyl lithium in hexane at a rate to keep the internal temperature below −70° C. The yellow solution was stirred 2 hours at this temperature, then treated with 46 mL of iodomethane and warmed to 0° C. After stirring 2 hours at 0° C., the mixture was poured into 1 L of saturated aqueous ammonium chloride and 1 L of ether. The phases were separated and the organic washed with water and brine and dried through sodium sulfonate. Removal of solvent in vacuo yielded 83 g of an orange oil which was 90% isopropyl 2-trifluoromethyl-6-methylbenzenesulfonate and 10% unreacted isopropyl 2-trifluoromethylbenzenesulfonate.

EXAMPLE 1B

Preparation of isopropyl 2-trifluoromethyl-6-methylbenzenesulfonate

A sample of 0.9 g sodium hydride 60% dispersion in mineral oil was washed with hexane to remove mineral oil, then suspended in 27 mL of tetrahydrofuran and cooled to 0° C. The suspension was treated with 3.1 mL isopropanol, then returned to room temperature and stirred until homogeneous. After re-cooling to 0° C., the mixture was treated with 5 g 2-trifluoromethylbenzenesulfonyl chloride. The mixture was poured into 50 mL of ether and 50 mL of water. The organic phase was dried through sodium sulfate and the solvent removed in vacuo to yield 4.04 g isopropyl 2-trifluoromethylbenzenesulfonate as an oil.

A solution of 4 g of isopropyl 2-trifluoromethylbenzenesulfonate in 40 mL of dry tetrahydrofuran was cooled to −78° C. under a static nitrogen atmosphere. To this was added 10.3 mL of a 1.6M solution of n-butyl lithium in hexane at a rate to keep the internal temperature below −70° C. The yellow solution was stirred 2 hours at this temperature, then treated with 1.8 mL of iodomethane and warmed to 0° C. After stirring 2 hours at 0° C., the mixture was poured into 40 mL of saturated aqueous ammonium chloride and 40 mL of ether. The phases were separated and the organic washed with water and brine and dried through sodium sulfate. Removal of solvent in vacuo yielded 3.3 g of an orange oil which was 90% isopropyl 2-trifluoromethyl-6-methylbenzenesulfonate and 10% unreacted isopropyl 2-trifluoromethylbenzenesulfonate.

EXAMPLE 1C

Preparation of isopropyl 2-trifluoromethyl-6-methylbenzenesulfonate

A solution of 6.2 g of 2-trifluoromethylbenzenesulfonyl chloride and 0.3 g of 4-dimethylaminopyridine in 30 mL of methylene chloride was cooled to 5° C. A solution of 2.2 g isopropanol and 3.7 g of triethylamine in 20 mL of methylene chloride was prepared and added dropwise to the solution of the sulfonyl chloride. The reaction mixture was returned to room temperature and allowed to stir for 3 hours. The mixture was treated with 200 mL of ether and washed with 60 mL of water. After removal of solvent in vacuo, 5.9 g of isopropyl 2-trifluoromethylbenzenesulfonate was isolated.

A solution of 4 g of isopropyl 2-trifluoromethylbenzenesulfonate in 40 mL of dry tetrahydrofuran was cooled to −78° C. under a static nitrogen atmosphere. To this was added 10.3 mL of a 1.6M solution of n-butyl lithium in hexane at a rate to keep the internal temperature below −70° C. The yellow solution was stirred 2 hours at this temperature, then treated with 1.8 mL of iodomethane and warmed to 0° C. After stirring 2 hours at 0° C., the mixture was poured into 40 mL of saturated aqueous ammonium chloride and 40 mL of ether. The phases were separated and the organic washed with water and brine and dried through sodium sulfate. Removal of solvent in vacuo yielded 3.3 g of an orange oil which was 90% isopropyl 2-trifluoromethyl-6-methylbenzenesulfonate and 10% unreacted isopropyl 2-trifluoromethylbenzenesulfonate.

EXAMPLE 2

Preparation of ethyl 2-trifluoromethyl-6-methylbenzenesulfonate

Ethyl 2-trifluoromethylbenzenesulfonate was made from 2-trifluoromethylbenzenesulfonyl chloride and treated first with butyl lithium and then with iodomethane in a manner analogous to that set forth above in Example 1A to yield ethyl 2-trifluoromethyl-6-methylbenzenesulfonate.

EXAMPLE 3

Preparation of ethyl 2-trifluoromethyl-6-ethylbenzenesulfonate

Ethyl 2-trifluoromethylbenzenesulfonate was made from 2-trifluoromethylbenzenesulfonyl chloride and treated first with butyl lithium and then with iodoethane in a manner analogous to that set forth above in Example 1A to yield ethyl 2-trifluoromethyl-6-ethylbenzenesulfonate.

EXAMPLE 4

Preparation of isopropyl 2-chloro-6-ethylbenzenesulfonate

Isopropyl 2-chlorobenzenesulfonate was made from 2-chlorobenzenesulfonyl chloride and treated first with butyl lithium and then with iodoethane in a manner analogous to that set forth above in Example 1A to yield isopropyl 2-chloro-6-ethylbenzenesulfonate.

EXAMPLE 5

Preparation of isopropyl 2-trifluoromethoxy-6-methylbenzenesulfonate

Isopropyl 2-trifluoromethoxybenzenesulfonate was made from 2-trifluoromethoxybenzenesulfonyl chloride and then treated first with butyl lithium and then with iodomethane in a manner analogous to that set forth above in Example 1A to yield isopropyl 2-trifluoromethoxy-6-methylbenzenesulfonate.

EXAMPLE 6

Preparation of isopropyl 2-trifluoromethyl-6-iodobenzenesulfonate

Isopropyl 2-trifluoromethylbenzene sulfonate was treated first with butyl lithium and then with 2,2,2-trifluoroethyl iodide in a manner analogous to that set forth above in Example 1A to yield isopropyl 2-trifluoromethyl-6-iodobenzenesulfonate.

EXAMPLE 7

Preparation of isopropyl 2-trifluoromethyl-6-n-propylbenzenesulfonate

Isopropyl 2-trifluoromethylbenzene sulfonate was treated first with butyl lithium and then with iodopropane in a manner analogous to that set forth above in Example 1A to yield isopropyl 2-trifluoromethyl-6-n-propylbenzenesulfonate.

EXAMPLE 8

Preparation of isopropyl 2-fluoro-6-methylbenzenesulfonate

Isopropyl 2-fluorobenzenesulfonate was made from 2-fluorobenzenesulfonyl chloride and treated first with butyl lithium and then with iodomethane in a manner analogous to that set forth above in Example to yield isopropyl 2-fluoro-6-methylbenzenesulfonate (formed as a 2:1 mixture with isopropyl 2-fluoro-3-methylbenzenesulfonate as the minor isomer).

EXAMPLE 25

Preparation of isopropyl 2-methyl-3,6-difluorobenzenesulfonate

Isopropyl 2,5-difluorobenzenesulfonate was made from 2,5-difluorobenzensulfonyl chloride and treated first with butyl lithium and then with iodomethane in a manner analogous to that set forth above in Example 1C to yield isopropyl 2-methyl-3,6-difluorobenzenesulfonate.

EXAMPLE 26

Preparation of isopropyl 2-ethyl-3,6-difluorobenzenesulfonate

Isopropyl 2,5-difluorobenzenesulfonate was made from 2,5-difluorobenzensulfonyl chloride and treated first with butyl lithium and then with iodoethane in a manner analogous to that set forth above in Example 1C to yield isopropyl 2-ethyl-3,6-difluorobenzenesulfonate.

EXAMPLE 27

Preparation of isopropyl 2-fluoro-6-trifluoromethoxybenzenesulfonate

Isopropyl 2-trifluoromethoxybenzenesulfonate was made from 2-trifluoromethoxybenzenesulfonyl chloride and treated first with butyl lithium and then with N-fluoro-O-benzenedisulfonimide in a manner analogous to that set forth above in Example 1B to yield isopropyl 2-fluoro-6-trifluoromethoxybenzenesulfonate.

EXAMPLE 28

Preparation of isopropyl 2-methyl-6-trifluoromethoxybenzenesulfonate

Isopropyl 2-trifluoromethoxybenzenesulfonate was made from 2-trifluoromethoxybenzenesulfonyl chloride and treated first with butyl lithium and then with iodomethane in a manner analogous to that set forth above in Example 1B to yield isopropyl 2-methyl-6-trifluoromethoxybenzenesulfonate.

EXAMPLE 29

Preparation of isopropyl 2-ethyl-6-trifluoromethoxybenzenesulfonate

Isopropyl 2-trifluoromethoxybenzenesulfonate was made from 2-trifluoromethoxybenzenesulfonyl chloride and treated first with butyl lithium and then with iodoethane in a manner analogous to that set forth above in Example 1B to yield isopropyl 2-ethyl-6-trifluoromethoxybenzenesulfonate.

EXAMPLE 30

Preparation of isopropyl 2-methoxymethyl-6-trifluoromethylbenzenesulfonate

Isopropyl 2-trifluoromethylbenzenesulfonate was made from 2-trifluoromethylbenzenesulfonyl chloride and treated first with butyl lithium and then with bromomethyl methyl ether in a manner analogous to that set forth in Example 1A to yield isopropyl 2-methoxymethyl-6-trifluoromethylbenzenesulfonate.

EXAMPLE 34

Preparation of isopropyl 2-methylthio-6-trifluoromethylbenzenesulfonate

Isopropyl 2-trifluoromethylbenzenesulfonate was prepared from 2-trifluoromethylbenzenesulfonyl chloride and treated first with butyl lithium and then with dimethyl disulfide in a manner analogous to that set forth in example 1A to yield isopropyl 2-methylthio-6-trifluoromethylbenzenesulfonate.

EXAMPLE 35

Preparation of isopropyl 2-ethylthio-6-methylbenzenesulfonate

Isopropyl 2-ethylthiobenzenesulfonate was prepared from 2-ethylthiobenzenesulfonyl chloride and treated first with butyl lithium and then with iodomethane in a manner analogous to that set forth in Example 1A to yield isopropyl 2-ethylthio-6-methylbenzenesulfonate.

EXAMPLE 36

Preparation of isopropyl 2-ethylthiobenzenesulfonate was prepared from 2-ethylthiobenzenesulfonyl chloride and treated first with butyl lithium and then with iodoethane in a manner analogous to that set forth in Example 1A to yield isopropyl 2-ethylthio-6-ethylbenzenesulfonate.

EXAMPLE 37

Preparation of isopropyl 2-ethylthio-6-fluorobenzenesulfonate

Isopropyl 2-ethylthiobenzenesulfonate was prepared from 2-ethylthiobenzenesulfonyl chloride and treated first with butyl lithium and then with N-fluoro-O-benzenedisulfonimide in a manner analogous to that set forth in Example 1A to yield isopropyl 2-ethylthio-6-fluorobenzenesulfonate.

EXAMPLE 38

Preparation of isopropyl 2-methylthio-6-methylbenzenesulfonate

Isopropyl 2-methylthiobenzenesulfonate was prepared from 2-methylthiobenzenesulfonyl chloride and treated first with butyl lithium and then with iodomethane in a manner analogous to that set forth in Example 1A to yield isopropyl 2-methylthio-6-methylbenzenesulfonate.

EXAMPLE 39

Preparation of isopropyl 2-ethyl-6-methylthiobenzenesulfonate

Isopropyl 2-methylthiobenzenesulfonate was prepared from 2-methylthiobenzenesulfonyl chloride and treated first with butyl lithium and then with iodoethane in a manner analogous to that set forth in Example 1A to yield isopropyl 2-ethyl-6-methylthiobenzenesulfonate.

EXAMPLE 40

Preparation of isopropyl 2-fluoro-6-methylthiobenzenesulfonate

Isopropyl 2-methylthiobenzenesulfonate was prepared from 2-methylthiobenzenesulfonyl chloride and treated first with butyl lithium and then with N-fluoro-O-benzenedisulfonimide in a manner analogous to that set forth in Example 1A to yield isopropyl 2-fluoro-6-methylthiobenzenesulfonate.

EXAMPLE 9

Preparation of sodium 2-trifluoromethyl-6-methylbenzenesulfonate

A solution of 83 g of the crude isopropyl 2-trifluoromethyl-6-methylbenzenesulfonate (which contained about 10% of isopropyl 2-trifluoromethylbenzenesulfonate) in 300 mL of tetrahydrofuran was treated with a solution of 24.8 g of 50% aqueous sodium hydroxide in 150 mL of water and heated to reflux for 4 hours, then stirred at room temperature overnight. The mixture was assayed by capillary GC (10 m DB-1, 100°–250° C. at 20° C./min) to ascertain that the isopropyl 2-trifluoromethyl-6-methylbenzenesulfonate was consumed. The tetrahydrofuran was removed in vacuo, then the remainder was poured into 100 mL of water and 200 mL of hexane. The aqueous phase was washed with hexane, then the water removed in vacuo to yield 71 g sodium 2-trifluoromethyl-6-methylbenzenesulfonate as a white solid.

EXAMPLES 10–15, 41–46 and 50–56

The sodium salts of Examples 10–15, 41–46 and 50–56 were made from the respective compounds of Examples 3–8, 25–30 and 34–40 in a manner analogous to that set forth above in Example 9:

| EX # | Compound |
|------|----------|
| 10 | Sodium 2-trifluoromethyl-6-ethylbenzenesulfonate |
| 11 | Sodium 2-chloro-6-ethylbenzenesulfonate |
| 12 | Sodium 2-trifluoromethoxy-6-methylbenzenesulfonate |
| 13 | Sodium 2-trifluoromethyl-6-iodobenzenesulfonate |
| 14 | Sodium 2-trifluoromethyl-6-n-propylbenzenesulfonate |
| 15 | Sodium 2-fluoro-6-methylbenzenesulfonate |
| 41 | Sodium 2-methyl-3,6-difluorobenzenesulfonate |
| 42 | Sodium 2-ethyl-3,6-difluorobenzenesulfonate |
| 43 | Sodium 2-fluoro-6-trifluoromethoxybenzenesulfonate |
| 44 | Sodium 2-methyl-6-trifluoromethoxybenzenesulfonate |
| 45 | Sodium 2-ethyl-6-trifluoromethoxybenzenesulfonate |
| 46 | Sodium 2-methoxymethyl-6-trifluoromethylbenzenesulfonate |
| 50 | Sodium 2-methylthio-6-trifluoromethylbenzenesulfonate |
| 51 | Sodium 2-ethylthio-6-methylbenzenesulfonate |
| 52 | Sodium 2-ethylthio-6-ethylbenzenesulfonate |
| 53 | Sodium 2-ethylthio-6-fluorobenzenesulfonate |
| 54 | Sodium 2-methylthio-6-methylbenzenesulfonate |
| 55 | Sodium 2-ethyl-6-methylthiobenzenesulfonate |
| 56 | Sodium 2-fluoro-6-methylthiobenzenesulfonate |

EXAMPLE 16

Preparation of 2-trifluoromethyl-6-methylbenzenesulfonyl chloride

A mixture of 290 g of sodium 2-trifluoromethyl-6-methylbenzenesulfonate and 500 mL of phosphorous oxychloride was heated to reflux for 5 hours. The mixture was then cooled to 0° C. and poured into a large flask containing 2000 g of ice and 2 L of ether. After stirring for 30 minutes, the phases were separated and the organic phase washed with cold water, cold saturated aqueous sodium carbonate, and then brine. The solvent was removed in vacuo to yield 2-trifluoromethyl-6-methylbenzenesulfonyl chloride as a brown oil.

EXAMPLES 17–22, 57–61 and 66–72

The sulfonyl chlorides of Examples 17–22, 57–61 and 66–72 were prepared from the respective compounds of Examples 10–15, 41–46 and 50–56 in a manner analogous to that set forth above for Example 16:

| EX # | Compound |
|------|----------|
| 17 | 2-trifluoromethyl-6-ethylbenzenesulfonate chloride |
| 18 | 2-chloro-6-ethylbenzenesulfonyl chloride |
| 19 | 2-trifluoromethoxy-6-methylbenzenesulfonyl chloride |
| 20 | 2-trifluoromethyl-6-iodobenzenesulfonyl chloride |
| 21 | 2-trifluoromethyl-6-n-propylbenzenesulfonyl chloride |
| 22 | 2-fluoro-6-methylbenzenesulfonyl chloride |
| 57 | 2-methyl-3,6-difluorobenzenesulfonyl chloride |
| 58 | 2-ethyl-3,6-difluorobenzenesulfonyl chloride |
| 59 | 2-fluoro-6-trifluoromethoxybenzenesulfonyl chloride |
| 60 | 2-methyl-6-trifluoromethoxybenzenesulfonyl chloride |
| 61 | 2-ethyl-6-trifluoromethoxybenzenesulfonyl chloride |
| 66 | 2-methylthio-6-trifluoromethylbenzenesulfonyl chloride |
| 67 | 2-ethylthio-6-methylbenzenesulfonyl chloride |
| 68 | 2-ethylthio-6-ethylbenzenesulfonyl chloride |
| 69 | 2-ethylthio-6-fluorobenzenesulfonyl chloride |
| 70 | 2-methylthio-6-methylbenzenesulfonyl chloride |
| 71 | 2-ethyl-6-methylthiobenzenesulfonyl chloride |
| 72 | 2-fluoro-6-methylthiobenzenesulfonyl chloride |

The composition and NMR data for the compounds of Examples 1–13, 15, 25, 27–30, 34, 44, 46 and 57–60 are set forth below in Table 1. All spectra were recorded at 200 MHz in CDCl$_3$ with TMS as an internal standard unless otherwise noted.

TABLE 1

Representative Compounds Produced by the Method of the Present Invention

[Structure: benzene ring with X (ortho), Z (ortho), Y (para), and SO₂OR₁ substituents]

| EX # | X | Y | R₁ | Z | 1H NMR Data (ppm) |
|---|---|---|---|---|---|
| 1 | CF₃ | H | CH(CH₃)₂ | CH₃ | 7.8 (m, 1H); 7.6 (m, 2H); 5.0 (m, 1H); 2.8 (s, 3H); 1.4 (d, 6H) |
| 2 | CF₃ | H | CH₂CH₃ | CH₃ | 7.8 (m, 1H); 7.6 (m, 2H); 4.2 (q, 2H); 2.8 (s, 3H); 1.4 (t, 3H) |
| 3 | CF₃ | H | CH₂CH₃ | CH₂CH₃ | 7.7 (m, 1H); 7.6 (m, 2H); 4.2 (q, 2H); 3.15 (q, 2H); 1.3 (m, 6H) |
| 4 | Cl | H | CH(CH₃)₂ | CH₂CH₃ | 7.45 (m, 2H); 7.3 (m, 1H); 4.9 (m, 1H); 3.15 (q, 2H); 1.35 (d, 6H); 1.3 (t, 3H) |
| 5 | OCF₃ | H | CH(CH₃)₂ | CH₃ | 7.5 (m, 1H); 7.3 (m, 2H); 5.0 (m, 1H); 2.75 (s, 3H); 1.4 (d, 6H) |
| 6 | CF₃ | H | CH(CH₃)₂ | I | 8.45 (m, 1H); 8.0 (m, 1H); 7.3 (m, 1H); 5.1 (m, 1H); 1.45 (d, 6H) |
| 7 | CF₃ | H | CH(CH₃)₂ | (CH₂)₂CH₃ | 7.7 (m, 1H); 7.6 (m, 2H); 5.0 (m, 1H); 3.1, (m, 2H); 1.7 (m, 2H); 1.35 (d, 6H); 1.0 (t, 3H) |
| 8 | F | H | CH(CH₃)₂ | CH₃ | as a 2:1 mixture with 2-fluoro-3-methyl isomer: 7.8 (m); 7.4 (m); 7.1 (m, 2H); 4.9 (m, 1H); 2.7 (s); 2.35 (d); 1.3 (d, 6H) |
| 9 | CF₃ | H | Na | CH₃ | D₂O: 7.6 (m, 1H); 7.35 (m, 2H); 2.5 (s, 3H) |
| 10 | CF₃ | H | Na | CH₂CH₃ | D₂O: 7.5 (m, 3H); 2.9 (q, 2H); 1.0 (t, 3H) |
| 11 | Cl | H | Na | CH₂CH₃ | D₂O: 7.1 (m, 3H); 2.85 (q, 2H); 1.0 (t, 3H) |
| 12 | OCF₃ | H | Na | CH₃ | D₂O: 7.1 (m, 3H); 2.4 (s, 3H) |
| 13 | CF₃ | H | Na | I | D₂O: 8.2 (m, 1H); 7.7 (m, 1H); 7.0 (m, 1H) |
| 15 | F | H | Na | CH₃ | D₂O, as a 2:1 mixture with 2-fluoro-3-methyl isomer: 7.45 (m); 7.25 (m); 7.0 (m,); 2.45 (s); 2.2 (d) |
| 25 | F | 5-F | CH(CH₃)₂ | CH₃ | 7.3 (m, 1H); 7.1 (m, 1H); 4.9 (m, 1H); 2.6 (s, 3H); 1.35 (d, 6H) |
| 27 | OCF₃ | H | CH(CH₃)₂ | F | 7.8 (m, 1H); 7.3 (2H); 5.1 (m, 1H); 1.4 (d, 6H) |
| 28 | OCF₃ | H | CH(CH₃)₂ | CH₃ | 7.5 (m, 1H); 7.3 (m, 2H); 5.0 (m, 1H); 2.75 (s, 3H); 1.4 (d, 6H) |
| 29 | OCF₃ | H | CH(CH₃)₂ | CH₂CH₃ | 7.6 (m, 1H); 7.3 (m, 2H); 5.0 (m, 1H); 3.2 (q, 2H); 1.4 (m, 9H) |
| 30 | CF₃ | H | CH(CH₃)₂ | CH₂OCH₃ | 8.1 (m, 1H); 7.8 (m, 2H); 5.05 (m, 1H); 4.95 (s, 2H); 3.5 (s, 3H); 1.4 (d, 6H) |
| 34 | CF₃ | H | CH(CH₃)₂ | SCH₃ | 7.6 (m, 5H); 5.1 (m, 1H); 2.6 (s, 3H); 1.4 (d, 6H) |
| 44 | OCF₃ | H | Na | CH₃ | D₂O: 7.2 (m, 3H); 2.4 (s, 3H) |
| 46 | CF₃ | H | Na | CH₂OCH₃ | D₂O: 7.5 (m, 3H); 4.8 (s, 2H); 3.2 (s, 3H) |
| 57 | F | 5-F | Cl | CH₃ | 7.5 (m, 1H); 7.2 (m, 1H); 2.7 (s, 3H) |
| 58 | F | 5-F | Cl | CH₂CH₃ | 7.5 (m, 1H); 7.2 (m, 1H); 3.2 (q, 2H); 1.3 (t, 3H) |
| 59 | OCF₃ | H | Cl | F | 7.8 (m, 1H); 7.3 (m, 2H) |
| 60 | OCF₃ | H | Cl | CH₃ | 7.7 (m, 1H); 7.4 (m, 2H); 2.9 (s, 3H) |

EXAMPLE 23

Preparation of di-O-isopropyl P-[[(2-trifluoromethyl-6-methylphenyl)sulfonyloxy]methyl]phosphonate A mixture of 100 mL of toluene, 11.6 g of 50% aqueous sodium hydroxide solution, and 10 mL of water was cooled in an ice bath and treated with 1.3 g of benzyltriethylammonium chloride and 12.0 g of diisopropyl P-(hydroxymethyl)phosphonate (prepared as in U.S. Pat. No. 5,272,128) and stirred vigorously. To this was added a solution of 15 g of the compound of Example 16 (2-trifluoromethyl-6-methylbenzenesulfonyl chloride) in 10 mL of toluene. The cooling bath was removed and the mixture stirred for one hour, then the layers were separated. The organic phase was washed with water (2×100 mL) and brine, then dried through calcium sulfate to yield 23 g of di-O-isopropyl P-[[(2-trifluoromethyl-6-methylphenyl)sulfonyloxy]methyl]phosphonate as a brown oil.

EXAMPLE 24

Preparation of O-isopropyl-O-methyl P-[[(2-trifluoromethyl-6-methylphenyl)sulfonyloxy]methyl]phosphonate A suspension of 11 g of phosphorus oxychloride in 100 mL of methylene chloride was treated with 20.1 g of di-O-isopropyl P-[[(2-trifluoromethyl-6-methylphenyl)sulfonyloxy]methyl]phosphonate in four portions, at a rate to keep the temperature below 28° C. After stirring overnight, the solvent was removed in vacuo to yield 19.5 g of crude O-isopropyl P-[[(2-trifluoromethyl-6-methylphenyl)sulfonyloxy]methyl]phosphonoyl chloride. A solution of 10 g of O-isopropyl P-[[(2-trifluoromethyl-6-methylphenyl)sulfonyloxy]methyl]phosphonoyl chloride in 50 mL of methylene chloride was treated with 0.1 g of dimethylaminopyridine and cooled to −50° C. A solution of 1.06 mL of dry methanol and 4.2 mL of triethylamine in 10 mL of methylene chloride was added dropwise to the first solution, then the mixture was allowed to return to room temperature and stirred overnight. The mixture was washed with water (2×50 mL) and brine and dried through calcium sulfate. Removal of solvent yielded 7.6 g of O-isopropyl-O-methyl P-[[(2-trifluoromethyl-6-methylphenyl)sulfonyloxy]methyl]phosphonate as a yellow oil.

The composition and NMR data for the compounds of Examples 23 and 24 are set forth below in Table 2. The spectra were recorded at 200 MHz in CDCl$_3$ with TMS as an internal standard.

TABLE 2

Representative Herbicides Produced by the Method of the Present Invention

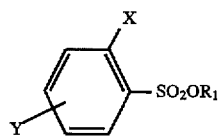

| Ex # | R$_2$ | R$_3$ | 1H NMR Data (ppm) |
|---|---|---|---|
| 23 | OCH(CH$_3$)$_2$ | OCH(CH$_3$)$_2$ | 7.8 (m, 1H); 7.6 (m, 2H); 4.75 (m, 2H); 4.2 (d, 2H); 2.8 (s, 3H); 1.3 (dd, 12H) |
| 24 | OCH$_3$ | OCH(CH$_3$)$_2$ | 7.8 (m, 1H); 7.65 (m, 2H); 4.8 (m, 1H); 4.3 (d, 2H); 3.8 (d, 3H); 2.85 (s, 3H); 1.35 (dd, 6H) |

It should be understood that the instant specification and examples are set forth by way of illustration and not limitation, and that various modifications and changes may be made without departing from the spirit and scope of the present invention as defined by the appended claims.

We claim:

1. A method for making a substituted benzene compound which comprises reacting a 2-substituted benzenesulfonate or a 2-substituted benzenesulfonate, further substituted in the 3, 4 or 5-position, with a lithium compound to form an intermediate compound; and reacting said intermediate compound with an electrophile to form a 2,6-disubstituted benzenesulfonate or a 2,6-disubstituted benzenesulfonate further substituted in the 3, 4 or 5-position, said 2-substituted benzenesulfonate or said 2-substituted benzenesulfonate further substituted in the 3, 4 or 5-position being a compound of the formula wherein R$_1$ is alkyl, cycloalkyl or phenyl;

X is any group that is not reactive with the lithium compound under the reaction conditions used; and Y is any group in the 3, 4 or 5-position that is not reactive with the lithium compound under the reaction conditions used.

2. The method of claim 1 wherein

R$_1$ is (C$_2$–C$_5$)alkyl;

X is fluoro, chloro, alkoxy, haloalkyl, haloalkoxy, alkyl, alkylthio, haloalkylthio, or N,N-dialkylcarboxamide; and Y is a hydrogen atom, fluoro, chloro, alkoxy, haloalkyl, haloalkoxy, alkylthio, or haloalkylthio.

3. The method of claim 2 wherein

R$_1$ is isopropyl;

X is fluoro, chloro, (C$_1$–C$_3$)alkoxy, halo(C$_1$–C$_3$)alkyl, halo(C$_1$–C$_3$)alkoxy, (C$_1$–C$_4$)alkyl, (C$_1$–C$_4$)alkylthio, halo(C$_1$–C$_4$)alkylthio, or N,N-di(C$_2$–C$_4$) alkylcarboxamide; and Y is a hydrogen atom, fluoro, chloro, (C$_1$–C$_3$)alkoxy, halo(C$_1$–C$_3$)alkyl, halo(C$_1$–C$_3$)alkoxy, (C$_1$–C$_4$) alkylthio, or halo(C$_1$–C$_4$)alkylthio.

4. The method of claim 3 wherein

X is chloro, fluoro, methoxy, trifluoromethyl, pentafluoroethyl, methylthio, ethylthio or trifluoromethoxy; and Y is a hydrogen atom, chloro, fluoro, methoxy, trifluoromethyl, trifluoromethoxy, pentafluoroethyl, methylthio, ethylthio, or trifluoromethylthio.

5. The method of claim 1, wherein the lithium compounds comprise elemental lithium, (C$_1$–C$_6$)alkyl lithiums and aryl lithiums.

6. The method of claim 5 wherein the lithium compound is selected from the group consisting of elemental lithium, methyl lithium, butyl lithium, hexyl lithium, phenyl lithium and thienyl lithium.

7. The method of claim 1 wherein the electrophile is selected form the group consisting of alkyl halides, haloalkyl alkyl ethers, aldehydes, ketones, alkyl sulfates, boron esters, alkyl disulfides, deuterium oxide, dimethylformamide, N-formylpiperidine, carbon dioxide, trialkylsilyl chlorides, and sources of positive halogens.

8. The method of claim 7 wherein the electrophile is selected from the group consisting of deuterium oxide, dimethylformamide, N-formylpiperidine, carbon dioxide, iodomethane, iodoethane, iodopropane, bromomethyl methyl ether, formaldehyde, benzaldehyde, benzophenone, dimethylsulfate, trimethyl borate, triisopropyl borate, methyl disulfide, ethyl disulfide, phenyl disulfide, trimethylsilyl chloride, N-fluorobenzenesulfonimide, N-fluoro-O-benzenedisulfonimide, N-fluoropyridinium salts, N-chlorosuccinimide and 2,2,2-trifluoroethyl iodide.

9. The method of claim 1 further comprising desulfonating the 2,6-disubstituted benzenesulfonate or the 2,6-disubstituted benzenesulfonate further substituted in the 3, 4 or 5-position to form a 1,3-disubstituted benzene or a 1,3-disubstituted benzene further substituted in the 4, 5 or 6-position.

10. The method of claim 1 further comprising hydrolyzing the 2,6-disubstituted benzenesulfonate or the 2,6-disubstituted benzenesulfonate further substituted in the 3, 4 or 5-position to form a 2,6-disubstituted benzenesulfonic acid or a salt of a 2,6-disubstituted benzenesulfonic acid, or the corresponding 2,6-disubstituted benzenesulfonic acid or the salt of a 2,6-disubstituted benzenesulfonic acid further substituted in the 3, 4 or 5-position.

11. The method of claim 1, wherein the method produces a mixture comprising the 2,6-disubstituted benzenesulfonate or the 2,6-disubstituted benzenesulfonate further substituted in the 3, 4 or 5-position and the 2substituted benzenesulfonate or the 2-substituted benzenesulfonate further substituted in the 3, 4 or 5-position, further comprising isolating the product mixture from the unreacted material by selectively hydrolyzing the 2,6-disubstituted benzenesulfonate or the 2,6-disubstituted benzenesulfonate further substituted in the 3, 4 or 5-position of the product mixture to form a salt of the 2,6-disubstituted benzenesulfonate or a salt of the 2,6-disubstituted benzenesulfonate further substituted in the 3, 4 or 5-position; partitioning the product mixture between an aqueous phase and an organic phase; and isolating the 2,6-disubstituted benzenesulfonate or the 2,6-disubstituted benzenesulfonate further substituted in the 3, 4 or 5-position salt from the aqueous phase.

12. The method of claim 10 further comprising converting the salt of a 2,6-disubstituted benzenesulfonic acid or a 2,6-disubstituted benzenesulfonic acid further substituted in the 3, 4 or 5-position to a 2,6-disubstituted benzenesulfonyl chloride or a 2,6-disubstituted benzenesulfonyl chloride further substituted in the 3, 4 or 5-position.

13. The method of claim 12 further comprising reacting the 2,6-disubstituted benzenesulfonyl chloride or the 2,6-disubstituted benzenesulfonyl chloride further substituted in the 3, 4 or 5-position with a hydroxymethylphosphorus compound to form a phosphosulfonate compound, said hydroxymethylphosphorus compound having the structural formula

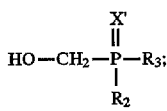

and said phosphosulfonate compound having the structural formula

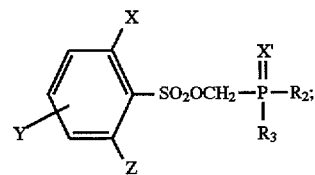

wherein

X is fluoro, chloro, alkoxy, haloalkyl, haloalkoxy, alkyl, alkylthio, haloalkylthio, or N,N-dialkylcarboxamide;

Y is a hydrogen atom, fluoro, chloro, alkoxy, haloalkyl, haloalkoxy, alkylthio, or haloalkylthio;

Z is alkyl, methyleneoxy, substituted methyleneoxy, boronic acid, alkylthio, a deuterium atom, formyl, carboxyl, trialkylsilyl or halo;

X' is oxygen or sulfur; and $R_2$ and $R_3$ are each independently substituted or unsubstituted alkyl, alkoxy, alkylthio, alkenyloxy, alkynyloxy, haloalkoxy, cyanoalkoxy, alkoxyalkoxy, cycloalkoxy, cycloalkylalkoxy, alkylideneiminooxy, chloro, amino, phenyl or phenoxy; or $R_2$ and $R_3$ are both alkoxy, taken together with the phosphorus atom to form a six-membered oxygen-containing ring.

* * * * *